(12) United States Patent
Pauly et al.

(10) Patent No.: US 8,507,288 B2
(45) Date of Patent: Aug. 13, 2013

(54) NITROGEN DIOXIDE SENSING APPARATUS AND METHOD USING CARBON NANOMATERIALS AS AN OZONE REMOVAL MATERIAL

(75) Inventors: Alain Pauly, Clermont-Ferrand (FR); Marc Dubois, Clermont-Ferrand (FR); Katia Guerin, Pont du Chateau (FR); André Hamwi, Clermont-Ferrand (FR); Jérôme Brunet, Riom (FR); Christelle Varenne, Chamalieres (FR); Bernard Lauron, Beaumont (FR)

(73) Assignees: Centre National de la Recherche Scientifique, Paris (FR); Universite Blaise Pascal—Clermont—Ferrand II, Clermont-Ferrand Cedex (FR)

( * ) Notice: Subject to any disclaimer, the term of this patent is extended or adjusted under 35 U.S.C. 154(b) by 351 days.

(21) Appl. No.: 12/995,630

(22) PCT Filed: May 27, 2009

(86) PCT No.: PCT/FR2009/000612
§ 371 (c)(1),
(2), (4) Date: Feb. 1, 2011

(87) PCT Pub. No.: WO2010/000956
PCT Pub. Date: Jan. 7, 2010

(65) Prior Publication Data
US 2011/0124112 A1 May 26, 2011

(30) Foreign Application Priority Data
Jun. 2, 2008 (FR) ...................................... 08 03006

(51) Int. Cl.
G01N 27/12 (2006.01)
G01N 27/04 (2006.01)
G01N 1/22 (2006.01)
G01N 33/00 (2006.01)
B01D 53/14 (2006.01)

(52) U.S. Cl.
USPC ................... 436/117; 95/47; 422/88; 422/90; 422/98; 436/116; 436/118; 436/135; 436/151; 436/174; 436/175; 436/177; 436/178; 436/181

(58) Field of Classification Search
USPC ..... 95/45, 47; 422/88, 90, 98; 436/116–118, 436/135, 151, 174–175, 177–178, 181
See application file for complete search history.

(56) References Cited

U.S. PATENT DOCUMENTS

| | | | | | |
|---|---|---|---|---|---|
| 3,677,708 | A | * | 7/1972 | Harman et al. | 436/117 |
| 3,999,122 | A | * | 12/1976 | Winstel et al. | 324/71.1 |
| 4,381,922 | A | * | 5/1983 | Frey et al. | 422/98 |
| 4,572,900 | A | * | 2/1986 | Wohltjen | 436/151 |
| 4,722,905 | A | * | 2/1988 | Honeybourne et al. | 436/151 |
| 5,015,590 | A | * | 5/1991 | Kinrade | 436/117 |
| 5,045,285 | A | * | 9/1991 | Kolesar, Jr. | 422/98 |
| 5,244,812 | A | * | 9/1993 | Honeybourne et al. | 436/164 |
| 5,536,473 | A | * | 7/1996 | Monkman et al. | 422/90 |
| 6,171,867 | B1 | * | 1/2001 | Feucht et al. | 436/124 |
| 2006/0189475 | A1 | | 8/2006 | Petrik et al. | |

FOREIGN PATENT DOCUMENTS

WO WO 2007/041550 4/2007

OTHER PUBLICATIONS

Hamamoto, O. et al, Bunseki Kagaku 1991, 40, 617-622.*
Uchiyama, S. et al, Electroanalysis 1993, 5, 121-124.*
Subrahmanyam, C. et al, Applied Catalysis B: Environmental 2005, 61, 98-106.*
Yan, N.-Q. et al, Industrial & Engineering Chemistry Research 2006, 45, 6420-6427.*
Picozzi, Ozone Absorption on Carbon Nanotubes: Ab initio Calculations and Experiments, J. Vac. Sci. Technol. A, 22, 1466-1470, 2004.
Viricelle, Selectivity Improvement of Semi-Conducting Gas Sensors by Selective Filter . . . , Materials Science and Engineering C, 26, 186-195, 2006.

* cited by examiner

*Primary Examiner* — Arlen Soderquist
(74) *Attorney, Agent, or Firm* — Morgan, Lewis & Bockius LLP

(57) ABSTRACT

The invention relates to the use of carbon nanomaterials as a filtration material pervious to nitrogen dioxide and impervious to ozone. The invention also relates to the use of carbon nanomaterials having a specific surface, measured by the BET method, of 15 to 40 $m^2/g$ inclusive and a form factor, equal to the ratio (highest dimension/lowest dimension) of the nanomaterial, of 5 to 250 inclusive, as material for filtering a gas mixture containing nitrogen dioxide and ozone, being pervious to the nitrogen dioxide and impervious to the ozone. The invention can be used in the field of air pollution.

15 Claims, No Drawings

NITROGEN DIOXIDE SENSING APPARATUS AND METHOD USING CARBON NANOMATERIALS AS AN OZONE REMOVAL MATERIAL

RELATED APPLICATIONS

The present application is a U.S. National Phase Application of International Application No. PCT/FR2009/000612 (filed May 27, 2009) which claims priority to French patent application Ser. No. 08/03006 (filed Jun. 2, 2008) which are hereby incorporated by reference in their entirety.

The invention relates to the use of carbon nanomaterials as a filtration material which is pervious to nitrogen dioxide and impervious to ozone. It also relates to a device and a method for detection and/or quantification of nitrogen dioxide in a gas mixture containing ozone and nitrogen dioxide.

The quality of air in industrialized cities is a worldwide concern.

Among all the pollutants, nitrogen dioxide represents a major problem in urban areas. That is because this pollutant is highly concentrated in city centers and contributes to the formation of another toxic gas, namely ozone. Yet above all, nitrogen dioxide has very harmful effects on human health. At concentrations as low as 15 ppb, nasal irritation, eye irritation and coughing are associated with exposure to nitrogen dioxide. At 30 ppb, hyperactivity of the respiratory muscles occurs. Above 80 ppb, an increased incidence of respiratory infections and throat diseases has been reported.

The directives given by the World Health Organization for exposure to nitrogen dioxide are 100 ppb during one hour and 75 ppb per day. In an urban environment, these values can be greatly exceeded. Thus, the quantity of nitrogen dioxide must be monitored continuously.

It has been proposed to detect and quantify nitrogen dioxide in ambient air by using a gas sensor microsystem based on a thin film of copper phthalocyanine.

This system is described in Brunet et al., Sensors & Actuators B130 (2008) 908-916.

This system comprises a sensor having a thin film of resistive semiconductor, in which the resistive semiconductor is copper phthalocyanine. Copper phthalocyanine is almost insensitive to reducing gases but highly sensitive to oxidizing gases such as nitrogen dioxide and ozone. The system described in this document, however, is an on-board system in vehicles. Yet in vehicles, ozone is non-existent and nitrogen dioxide is the only oxidizing pollutant, which makes it possible for the system described in this article to measure nitrogen dioxide with precision and selectivity.

In fact, it is mentioned in this article that the sensor consisting of a thin film of copper phthalocyanine does not allow selective monitoring and quantification of nitrogen dioxide in the presence of ozone, and that in this case it is necessary to filter out the ozone before passing air over the sensor with thin films of copper phthalocyanine.

Thus, Viricelle et al. in "Selectivity improvement of semi-conducting gas sensors by selective filter for atmospheric pollutants detection", Materials Science and Engineering C, vol. 26, Issues 2-3, March 2006, 186-195, have proposed a system for selective measurement of nitrogen dioxide in a gas mixture containing nitrogen dioxide and ozone, comprising a sensor with a thin film of semiconductor which is either tin oxide, $SnO_2$ or copper phthalocyanine, this filter comprising, before the semiconductor sensor, a filter consisting of manganese oxide, $MnO_2$, when the semiconductor is tin oxide, or consisting of indigo when the semiconductor is copper phthalocyanine.

With the semiconductor device comprising $SnO_2$ and an $MnO_2$ filter, however, the ozone was eliminated well but the sensitivity to nitrogen dioxide was also reduced. The system with a thin film of copper phthalocyanine semiconductor and a filter filled with indigo, on the other hand, had a high selectivity with respect to $NO_2$.

However, ozone reacts irreversibly with indigo, as shown in Viricelle et al., "Selectivity improvement of semi-conducting gas sensors by selective filter for atmospheric pollutants detection", Materials Science and Engineering C, Elsevier Science S.A., vol. 26, Nos. 2-3, 1 Mar. 2006 (2006-03-01), pages 186-195.

This leads to consumption of the filter over the course of time, reducing its lifetime.

It is an object of the invention to overcome the drawbacks of the systems for selective detection and/or quantification of nitrogen dioxide in a gas mixture containing nitrogen dioxide and ozone, by providing a potentially regenerable filtration structure having limited interaction with the surface of the active material.

To this end, the invention provides the use of carbon nanomaterials having:
  a specific surface, measured by BET, of between 15 and 40 $m^2/g$ inclusive,
  a form factor equal to the ratio (largest dimension/smallest dimension) of the nanomaterial of between 5 and 250 inclusive,
as a material, pervious to nitrogen dioxide and impervious to ozone, for filtration of a gas mixture containing nitrogen dioxide and ozone.

Preferably, the nanomaterials have a specific surface, measured by BET, of between 19 and 30 $m^2/g$ inclusive.

In a first preferred embodiment of the use of the invention, the nanomaterials comprise 70% by weight of nanodisks and 30% by weight of nanocones of carbon, said mixture having a specific surface, measured by BET, of between 26 and 30 $m^2/g$ inclusive.

In a second preferred embodiment of the use of the invention, the nanomaterials are nanofibers having a specific surface, measured by BET, of 19 $m^2/g$ and a form factor equal to the ratio (length/diameter) of 250.

The gas mixture is preferably air.

The invention also provides a system for selective detection and/or quantification of nitrogen dioxide in a gas mixture containing nitrogen dioxide and ozone, of the type comprising a resistive gas sensor based on a thin film of organic semiconductor which reacts with nitrogen dioxide and ozone, characterized in that it comprises, upstream of said sensor, a device for filtration of said gas mixture comprising carbon nanomaterials having a specific surface, measured by BET, of between 15 and 40 $m^2/g$ inclusive and a form factor equal to the ratio (largest dimension/smallest dimension) of the nanomaterial of between 5 and 250 inclusive.

In the invention, a thin film is intended to mean a layer with a thickness of between 10 and 500 nanometers, preferably between 100 and 500 nanometers.

Preferably, the nanomaterials have a specific surface of between 19 and 30 $m^2/g$ inclusive.

In a first preferred embodiment of the system of the invention, the nanomaterials are nanofibers having a specific surface of 19 $m^2/g$ and a form factor equal to the ratio (length/diameter) of 250.

In a second preferred embodiment of the system of the invention, the nanomaterials comprise a mixture of 70% by weight of nanodisks and 30% by weight of nanocones, said mixture having a specific surface of between 26 and 30 $m^2/g$ inclusive.

In all the embodiments, in the system of the invention, the sensor is preferably a sensor based on a thin film of copper phthalocyanine.

Likewise, preferably, the gas mixture is air.

The invention provides a method for selective detection and/or quantification of nitrogen dioxide in a gas mixture containing nitrogen dioxide and ozone, of the type comprising passage of said gas mixture through a filter, then of the filtered gas over a resistive gas sensor based on a thin film of organic semiconductor which reacts with nitrogen dioxide and ozone, characterized in that it comprises passage of the gas through a filter containing carbon nanomaterials having a specific surface, measured by BET, of between 15 and 40 $m^2/g$ inclusive and a form factor equal to the ratio (largest dimension/smallest dimension) of the carbon nanomaterial of between 5 and 250 inclusive.

Preferably, in the method of the invention, the nanomaterials have a specific surface of between 19 and 30 $m^2/g$ inclusive.

In a first preferred embodiment of the method of the invention, the nanomaterials are nanofibers having a specific surface of 19 $m^2/g$ and a form factor equal to the ratio (diameter/thickness) equal to 250.

In a second preferred embodiment of the method of the invention, the nanomaterials comprise a mixture of 70% by weight of nanodisks and 30% by weight of nanocones, said mixture having a specific surface of between 26 and 30 $m^2/g$ inclusive.

The invention will be better understood, and other advantages and characteristics of it will be more clearly apparent, on reading the following explanatory description.

The invention is based on the discovery that certain carbon nanomaterials have the capacity to filter ozone selectively.

These nanomaterials are furthermore regenerable, as taught by M. Chesneau, in the chapter entitled "Applications du carbone: les matériaux carbones activés" [Applications of carbon: activated carbon materials], in the work: Le carbone dans tous ses états [Carbon in all its states], Editors: P. Bernier and S. Lefrant, Gordon and Breach Science Publishers, 1997.

In the context of the invention, the terms "carbon nanomaterials" mean materials of which at least one dimension lies between 1 nanometer and 350 nanometers.

The nanomaterials may be nanoparticles, nanofibers, nanocones, nanodisks or single- or multi-walled nanotubes, or mixtures thereof.

Carbon nanomaterials are nanomaterials made of carbon having or not having a graphite structure.

For use as ozone-selective filtration material for a gas mixture containing nitrogen dioxide and ozone, the carbon nanomaterials may be either nanofibers or nanocones, nanodisks or nanotubes, or alternatively nanoparticles of carbon.

Mixtures of such nanomaterials may also be employed in the use of the invention.

In the invention, an "ozone-selective filtration material" is intended to mean a filtration material which is impervious to ozone, that is to say it retains ozone, and which is pervious to nitrogen dioxide, that is to say it lets nitrogen dioxide pass through.

It is the characteristics of the specific surface and form factor of the carbon nanomaterials used in the invention which make such a filtration material ozone-selective.

In order to determine this specific surface and this form factor, various carbon materials were tested.

These carbon materials were on the one hand carbon materials which were not nanomaterials, that is to say graphite particles having an average size measured by laser granulometry of 4 μm, and a sample of MAXSORB active carbon, which is an active carbon marketed by Kansai Coke and Chemical Co, Japan, and on the other hand nanofibers, nanotubes and mixtures of nanodisks and nanocones of carbon.

The nanofibers tested were:

carbon nanofibers, denoted below as CNF, obtained by chemical vapor deposition (CVD) then heat-treated at 1800° C., supplied by the company MER Corporation, having a specific surface, measured by BET, of 19 $m^2/g$, having a diameter of between 80 and 350 nanometers and a length of between 2000 nanometers and 20,000 nanometers, that is to say a length/diameter form factor of between 5.7 and 250.0 and having a purity of 90%, and the same nanofibers which had undergone grinding in a stainless steel ball grinder for:

20 min in air. These nanofibers are denoted below as CNFg20 and have a specific surface, measured by BET, of 43 $m^2/g$, 60 min in air. These nanofibers are denoted below as CNFg60 and have a specific surface, measured by BET, of 87 $m^2/g$, 12 h in air. These nanofibers are denoted below as CNF12h air and have a specific surface, measured by BET, of 505 $m^2/g$, and 12 h in argon. These nanofibers are denoted below as CNF12h Ar and have a specific surface of 397 $m^2/g$.

Grinding the nanofibers induces rupture of the fibers, which is proportional to the grinding time. After 12 h, the fibrillary nature has disappeared, leaving instead grains of the order of 1 micron formed by the aggregation of broken fibers.

The carbon nanocones and nanodisks tested were a mixture of 70% by mass of nanodisks, 20% by mass of nanocones and 10% by mass of amorphous carbon, a mixture supplied by N-TEC Norway, in which mixture the nanodisks have a diameter of between 800 nanometers and 3200 nanometers and a thickness of between 15 nanometers and 65 nanometers, and the nanocones have a diameter of between 500 nanometers and 2800 nanometers and a thickness of between 15 and 65 nanometers, which corresponds to a form ratio of between 12.3 and 213.3 for the nanodisks and a form ratio of between 7.7 and 186.7 inclusive for the nanocones.

This mixture of nanocones, nanodisks and amorphous carbon had a specific surface, measured by BET, of 30 $m^2/g$. The same mixture of nanocones and nanodisks, which were washed, was also tested. The washing consisted in washing with an excess of dimethyl sulfoxide for 30 min in a bath with ultrasound, and its purpose was to solubilize the uncracked heavy oil residues deposited on the surface of the nanodisks and nanocones. The carbon is separated from the solvents, which takes on a yellow coloration, by centrifuging at 10,000 rpm, and finally the solvent is evaporated at 150° C.

After this washing, the mixture of nanocones, denoted below as washed CND, had a specific surface of 26 $m^2/g$.

The nanotubes tested were single-walled nanotubes, denoted below as SWCNT, obtained by the electric arc method, and supplied by the company NANOLEDGE. These single-walled nanotubes have a high proportion of defects. They contain 12% by mass of metal catalysts, 25% by mass of amorphous carbon and approximately 10% of nanoparticles with a graphite structure. These single-walled nanoparticles had a specific surface of 165 $m^2/g$.

The graphite tested was a graphite powder having a specific surface of 7 $m^2/g$. This sample is denoted as graphite in the table below.

The active carbon, denoted below as MAXSORB, consisted of carbon particles with an average diameter of 1 μm and had a specific surface, measured by BET, of 3000 $m^2/g$.

The test conditions were as follows: ozone concentrations of between 0 and 300 ppb in a mixture with from 0 to 300 ppb of nitrogen dioxide were introduced into dried clean air. These gas mixtures were introduced with a total flow rate of 45 liters/hour into a chamber with a volume of 0.88 cm$^3$ containing 200 mg of each of the filtration materials mentioned above. The filtered gas mixture was then measured for both nitrogen dioxide and ozone by commercial gas analyzers, one analyzing ozone and the other analyzing nitrogen dioxide.

The filtration power of the filtration material tested is denoted below as η and is equal to the following equation:

$$\eta = 100 \times \left( \frac{C_{upstream} - C_{downstream}}{C_{upstream}} \right)$$

It can be seen from this formula that η tends toward 100 when the ozone is retained on the filtration material, and η for ozone tends toward 0 when it is not retained by the material and therefore passes through the filtration material, that is to say it does not fulfill its function as an ozone-selective filtration material.

The filtration material of the invention must be impervious to $O_3$ but pervious to $NO_2$. For this reason, the η for $NO_2$ should tend toward 0.

In other words, the filtration material if totally ozone-selective and totally pervious to $NO_2$ should have an η ozone equal to 100 and an η $NO_2$ equal to 0.

The results obtained are collated in Table 1 below:

TABLE 1

| Filtering material | MAXSORB sample | Graphite sample | CNFg20 | CNFg60 | CNF12h air | CNF12h Ar | CNF | CND | Washed CND | SWCNT |
|---|---|---|---|---|---|---|---|---|---|---|
| SS (m$^2$/g) | 1500 | 7 | 43 | 87 | 505 | 397 | 19 | 30 | 26 | 165 |
| η $O_3$ | 91.0 | 29.1 | 93.9 | 95.9 | 97.5 | 97.4 | 91.6 | 98.7 | 96.7 | 98.6 |
| η $NO_2$ | 91.0 | 49.6 | 36.2 | 71.6 | 32.3 | 50.4 | ~0 | 5.0 | 3.2 | 54.2 |

It can be seen from Table 1 that the samples CNF CND and washed CND, which have a specific surface, measured by BET, of between 19 and 30 m$^2$/g inclusive, retain more than 90% of the ozone while retaining less than 5% of the nitrogen dioxide. Conversely, when the specific surface is 43 m$^2$/g, as is the case for the sample denoted as CNFg20, the filtering power of these nanofibers for ozone is 93.9, that is to say greater than the ozone filtering power of the sample denoted as CNF, but the material CNFg20 also retains 36% of nitrogen dioxide, which makes it an unsuitable material.

For these reasons, the nanomaterials used as an ozone-selective filtration material have a specific surface, measured by BET, of between 15 and 40 m$^2$/g inclusive, and preferably between 19 and 30 m$^2$/g inclusive.

The specific surface of the material, however, is not the only factor in the filtering power of the carbon nanomaterial. The form factor is also important, because it is this which allows the filtration material to fully exert a filtering action.

Thus, in a preferred embodiment, the carbon nanomaterials used as an $O_3$-selective filtration material comprise carbon nanofibers having a specific surface of 19 m$^2$/g and a form factor, equal to the length/diameter ratio, of between 5 and 250 inclusive, and more preferably 250.

In another preferred embodiment of the invention, the $O_3$-selective filtration material used in the invention is composed of a mixture of 70% by weight of nanodisks, 20% by weight of nanocones and 10% by weight of washed or unwashed amorphous carbon, having a specific surface of between 26 and 30 m$^2$/g, the nanodisks having a form ratio of between 12.3 and 213.3 inclusive, preferably 213.3, and the nanocones having a form factor of between 7.7 and 186.7, preferably equal to 186.7.

In a preferred embodiment of the invention, the filtration material of the invention is used as a material filling a filter placed upstream of a resistive gas sensor based on a thin film of organic semiconductor which reacts with nitrogen dioxide and ozone, in order to form a system for selective detection and/or quantification of the nitrogen dioxide in a gas mixture containing nitrogen dioxide and ozone.

A resistive sensor based on thin films of suitable semiconductor is, in particular, a sensor based on thin films of copper phthalocyanine.

This is because copper phthalocyanine is almost insensitive to reducing gases and highly sensitive to oxidizing gases, and in particular ozone and nitrogen dioxide. By ozone-selective filtering of the gas mixture, by virtue of the filtration device containing the filtration material of the invention, before it passes over the sensor, the ozone is eliminated and only the nitrogen dioxide will be detected and quantified.

The gas mixture is more particularly air.

Thus, a method for selective detection and/or quantification of nitrogen dioxide in a gas mixture, in particular air, containing nitrogen dioxide and $O_3$ comprises a step of passing said gas mixture through a filter containing carbon nanomaterials according to the invention.

The nanomaterials of the invention may also be used in all systems and in all methods for selective detection and quantification of nitrogen dioxide, optionally with a sensor other than a sensor based on a thin film of copper phthalocyanine, as will be apparent to the person skilled in the art.

Furthermore, the nanomaterials of the invention may be functionalized in order to increase their power of filtering ozone selectively with respect to nitrogen dioxide, for example by functionalizing them with materials that are very selective with respect to ozone, for example indigo, or by styrene or acrylonitrile functions, by creating a chemical bond between the nanomaterials and the functionalization group.

In general, the functionalization group is an organic group having at least one double bond for grafting onto the carbon of the carbon nanomaterials, and at least one other unsaturated double or triple bond for increasing the ozone-selective filtration power of the carbon materials.

Functionalization with indigo may also be applied by physical grafting. In this case, the interactions between the indigo molecule and the nanocarbon surface are of the Van der Waal type (pi-stacking).

More precisely, a solution of acetonitrile saturated with indigo is brought in contact with the nanocarbon powder (CNDs treated at 2600° C. in order to increase the degree of graphitization, CNF) then the mixture is sonified for 20 minutes. After decoloration of the solution and settling of the nanocarbon, the supernatant liquid is removed. The powder obtained is placed in a primary vacuum at 100° C. for 12 hours in order to remove the traces of solvent. The decoloration of the solution is quantified by UV-visible spectrometry (Lambda=600 nm: maximum absorbance wavelength of indigo).

This functionalization by pi-stacking is favored for nanocarbons which are post-treated at high temperatures in order to increase their level of graphitization (1800 and 2600° C. for nanofibers and mixtures of nanocones and nanodisks, respectively). The absorbent power of mixtures of nanocones and nanodisks after having undergone a heat treatment at 2600° C. is 52 mg of indigo per gram of carbon.

The invention claimed is:

1. A method for filtration of a gas mixture containing nitrogen dioxide and ozone comprising filtering the gas mixture through carbon nanomaterials having:
   a specific surface, measured by BET, of between 15 and 40 $m^2/g$ inclusive,
   a form factor equal to the ratio (largest dimension/smallest dimension) of the nanomaterial of between 5 and 250 inclusive,
as a material, pervious to nitrogen dioxide and impervious to ozone.

2. The method as claimed in claim 1, characterized in that the nanomaterials have a specific surface of between 19 and 30 $m^2/g$ inclusive.

3. The method as claimed in claim 1, characterized in that the nanomaterials comprise 70% by weight of nanodisks and 30% by weight of nanocones of carbon, said mixture having a specific surface, measured by BET, of between 26 and 30 $m^2/g$ inclusive.

4. The method as claimed in claim 1, characterized in that the nanomaterials are carbon nanofibers having a specific surface, measured by BET, of 19 $m^2/g$ and a form factor equal to the ratio (length/diameter) of 250.

5. The method as claimed in claim 1, characterized in that the gas mixture is air.

6. A system for selective detection and/or quantification of nitrogen dioxide in a gas mixture containing nitrogen dioxide and ozone, of the type comprising a resistive gas sensor based on a thin film of organic semiconductor which reacts with nitrogen dioxide and ozone, characterized in that it comprises, upstream of said sensor, a device for filtration of said gas mixture comprising carbon nanomaterials having a specific surface, measured by BET, of between 15 and 40 $m^2/g$ inclusive and a form factor equal to the ratio (largest dimension/smallest dimension) of said nanomaterial of between 5 and 250 inclusive.

7. The system as claimed in claim 6, characterized in that the nanomaterials have a specific surface of between 19 and 30 $m^2/g$ inclusive.

8. The system as claimed in claim 6, characterized in that the nanomaterials are nanofibers having a specific surface of 19 $m^2/g$ and a form factor equal to the ratio (length/diameter) equal to 250.

9. The system as claimed in claim 6, characterized in that the nanomaterials comprise a mixture of 70% by weight of nanodisks and 30% by weight of nanocones, said mixture having a specific surface of between 26 and 30 $m^2/g$ inclusive.

10. The system as claimed in claim 6, characterized in that the sensor is a sensor based on a thin film of copper phthalocyanine.

11. The system as claimed in claim 6, characterized in that the gas mixture is air.

12. A method for selective detection and/or quantification of nitrogen dioxide in a gas mixture containing nitrogen dioxide and ozone, of the type comprising passage of said gas mixture through a filter, then of the filtered gas over a resistive gas sensor based on a thin film of organic semiconductor which reacts with nitrogen dioxide and ozone, characterized in that it comprises passage of the gas mixture through a filter containing carbon nanomaterials having a specific surface, measured by BET, of between 15 and 40 $m^2/g$ inclusive and a form factor equal to the ratio (largest dimension/smallest dimension of between 5 and 250 inclusive.

13. The method as claimed in claim 12, characterized in that the nanomaterials have a specific surface of between 19 and 30 $m^2/g$ inclusive.

14. The method as claimed in claim 12, characterized in that the nanomaterials are nanofibers having a specific surface of 19 $m^2/g$ and a form factor equal to the ratio (length/diameter) equal to 250.

15. The method as claimed in claim 12, characterized in that the nanomaterials comprise a mixture of 70% by weight of nanodisks and 30% by weight of nanocones, said mixture having a specific surface of between 26 and 30 $m^2/g$ inclusive.

* * * * *